(12) United States Patent
Pinard et al.

(10) Patent No.: US 12,146,188 B2
(45) Date of Patent: Nov. 19, 2024

(54) METHOD COMBINING SINGLE CELL GENE EXPRESSION MAPPING AND TARGETED RNA OR c-DNA SEQUENCING USING PADLOCK OLIGONUCLEOTIDES COMPRISING A BARCODE REGION

(71) Applicant: Miltenyi Biotec B.V. & Co. KG, Bergisch Gladbach (DE)

(72) Inventors: Robert Pinard, Lowell, MA (US); Seiyu Hosono, Stoneham, MA (US)

(73) Assignee: Miltenyi Biotec B.V. & Co. KG, Bergisch Gladbach (DE)

( * ) Notice: Subject to any disclaimer, the term of this patent is extended or adjusted under 35 U.S.C. 154(b) by 632 days.

(21) Appl. No.: 17/345,011

(22) Filed: Jun. 11, 2021

(65) Prior Publication Data

US 2021/0403992 A1  Dec. 30, 2021

(30) Foreign Application Priority Data

Jun. 29, 2020 (EP) .................................... 20182775

(51) Int. Cl.
*C12P 19/34* (2006.01)
*C12Q 1/6825* (2018.01)
*C12Q 1/6869* (2018.01)

(52) U.S. Cl.
CPC .......... *C12Q 1/6869* (2013.01); *C12Q 1/6825* (2013.01)

(58) Field of Classification Search
CPC .. C12Q 1/6869; C12Q 1/6825; C12Q 1/6853; C12Q 1/6841
See application file for complete search history.

(56) References Cited

U.S. PATENT DOCUMENTS 10,174,366 B2 * 1/2019 Landegren ........... C12Q 1/6804

FOREIGN PATENT DOCUMENTS

WO  WO 2017/081049 A1  5/2017
WO  WO 20199/068880 A1  4/2019

OTHER PUBLICATIONS

"Xiaoyin Chen, High-Throughput Mapping of Long-Range Neuronal Projection Using in Situ Sequencing, Oct. 2019, vol. 179, Issue 3, pp. 772-786.e19" (Year: 2019).*
"Eng, CH.L., Lawson, M., Zhu, Q et al. Transcriptome-scale super-resolved imaging in tissues by RNA seqFISH+, Mar. 2019, Nature 568, 235-239." (Year: 2019).*
"Lemin Zhang et al., Detecting DNA-binding of proteins in vivo by UV-crosslinking and immunoprecipitation, Jul. 2004, Biochemical and Biophysical Research Communications 322, 705-711." (Year: 2014).*
Highly Sensitive Detection of Uracil-DNA Glycosylase Activity Based on Self-Initiating Multiple Rolling Circle Amplification (Year: 2019).*
Chen Xiaoyin et al, "High throughput Mapping og Long-Range Neuronal Projection Using in Sity Sequencing," Cell, Elsevier, Amsterdam NL vol. 179 No. 3, Oct. 17, 2019, p. 772-774 F.
N. Maino- et al. "A microfluidic platform towards automated multiplexed in situ sequencing", Scientific Reports vol. 9, No. 1, Mar. 5, 2019 whole document.

* cited by examiner

*Primary Examiner* — Kenneth R Horlick
(74) *Attorney, Agent, or Firm* — Jaquelin K. Spong

(57) ABSTRACT

Microscopy imaging that allow for multiple mRNAs to be resolved at a single cell level provides valuable information regarding transcript amount and localization, which is a crucial factor for understanding tissue heterogeneity, the molecular development and treatment of diseases. The current invention describes a method (Fly FISH) which combined the use of padlock oligonucleotides as fluorescence in situ hybridization (FISH) probes for detection and sequencing targeted portion of RNA or cDNA transcript at a cellular level with less limitation in the amount of transcripts and the length of the sequence that can be analyzed. Padlocks probes containing various barcodes in their core are utilized both as FISH probes and also to capture RNA portion that can be sequenced. The same barcodes can be used to selectively prime a rolling circle amplification and amplify a subset of transcripts coming from a specific region that have been tagged as of interest during the probing steps.

13 Claims, 7 Drawing Sheets

METHOD COMBINING SINGLE CELL GENE EXPRESSION MAPPING AND TARGETED RNA OR c-DNA SEQUENCING USING PADLOCK OLIGONUCLEOTIDES COMPRISING A BARCODE REGION

CROSS REFERENCE TO RELATED APPLICATIONS

This non-Provisional US Patent Application claims priority to European patent application serial number EP20182775.5 filed in the European Patent Office on Jun. 29, 2020. This prior application is incorporated by reference in its entirety.

STATEMENT REGARDING FEDERALLY SPONSORED RESEARCH

Not applicable.

STATEMENT REGARDING MICROFICHE APPENDIX

Not applicable.

BACKGROUND

The present invention relates to a method for sequencing and localizing RNA or c-DNA strands by selective amplification of padlock oligonucleotides comprising a barcode region.

Padlock oligonucleotides have proven to be very successful in polymerizing short portion of nucleic acids to which it has been hybridized to. Most padlock approaches begin by reverse transcribing the target into cDNA.

Padlock methods are for example disclosed in "Highly multiplexed subcellular RNA sequencing in situ" by Lee et al., Science. 2014 Mar. 21; 343(6177): 1360-1363. doi: 10.1126/science.1250212 or "Efficient In Situ Detection of mRNAs using the Chlorella virus DNA ligase for Padlock Probe Ligation" by Nils Schneider and Matthias Meier; Feb. 5, 2020—Cold Spring Harbor Laboratory Press A comprehensive assay for targeted multiplex amplification of human DNA sequences is published by Sujatha Krishnakumar et al.; PNAS sent for review Feb. 19, 2008.

Further, WO2017143155A2 discloses multiplex alteration of cells using a pooled nucleic acid library and analysis thereof and WO2018045181A1 discloses Methods of generating libraries of nucleic acid sequences for detection via fluorescent in situ sequencing The published Padlock methods allow sequencing of DNA or RNA, but do not give any information from what specific cell or tissue location the sequenced DNA or RNA origins from.

Microscopy imaging that allow for multiple mRNAs to be resolved at a single cell level provides valuable information regarding transcript amount and localization, which is a crucial factor for understanding tissue heterogeneity, the molecular development and treatment of diseases.

Fluorescence in situ hybridization (FISH)-based methods allow for transcripts to be directly labelled in tissue sections and for spatial information to be captured. However, the numbers of probes that can be used is limited and overlap of fluorescence signals is often an issue. Moreover, the optical resolution of confocal microscopy limits often are reached and therefore the amount of probes that can be detected concomitantly is reduced. SeqFISH+, is an approach that does not use probes already labelled with fluorophores but rather uses transcript-specific ones that contain barcode sequences which serve as target sites for fluorescently labelled secondary probes. The various target-specific probes are identified using secondary probes that bind to these barcode sites during sequential rounds of probing. By limiting the amount of probes that are detected by the secondary probes a limited amount are fluorescing and therefore the signal can be discernible. Multiple separated images are collected and aggregated computationally to create a composite high-resolution image without requiring high resolution instrument microscope.

However, although these approaches allow for the evaluation of several genes simultaneously, the sequence information of the transcript is not captured. Other methods based on single-cell RNA sequencing (scRNA-seq) can profile whole transcriptomes and capture the sequence information. However, the original location at the tissue or single cell level is often also missing. A method where both sequence and spatial information is be captured at a resolution approaching the single-cell remains a difficult challenge. Some approaches have use FISSEQ and BaristaSeq (another gap-filling padlock based approach to achieve that task with a limited read-length of about 15 bases.

SUMMARY OF THE INVENTION

Object of the invention is a method for single cell gene expression mapping and targeted RNA or c-DNA sequencing of a sample comprising at least one RNA or c-DNA strand comprising the steps
  a. providing a oligonucleotide having a 5' and a 3' end combined by 50-1000 nucleic acids that are complementary to the at least one RNA or c-DNA strand of the sample wherein the oligonucleotide comprises at least one barcode region with 2-20 nucleotides
  b. hybridizing the oligonucleotide at the 5' and the 3' ends to complementary parts of the at least one RNA or c-DNA strand to create a padlock with a gap between the 5' and the 3' end of the padlock
  c. filling the gap of the padlock with the complementary nucleotides and ligate them to generate a single strand circular template and wherein the single strand circular template is provided with at least one detection probe capable of binding to at least a part of the barcode region
  d. multiplying the single strand circular template by a polymerase capable of rolling circle amplification into a plurality of DNA concatemers forming a rolony
  e. determining the spatial localisation of the single strand circular template
  f. determining the sequence of the single strand circular template characterized in that
  the detection probe comprises a oligonucleotide with 2 to 20 nucleotides capable of binding to at least a part of the barcode region and a detection region selected from the group comprising a magnetic particle, a fluorescence dye, a radioactive label or an antigen binding moiety.

In the present invention, the known gap-fill padlock technology is modified by using padlocks that are tethered to a detection probe, preferably an antigen binding moiety. The detection probe can optionally be crosslinked to the tissue. The padlocks can then be released from the detection probe and hybridized to a specific portion of a messenger RNA directly on a section of tissue that has been fixed and permeabilized.

In a variant of the invention, step e) and f) can be performed at the padlock instead of the single strand circular template.

BRIEF DESCRIPTION OF THE DRAWINGS

The drawings shall explain the method of the invention and its embodiments without limiting the scope of the claims.

DETAILED DESCRIPTION

The invention is now described with respect FIGS. 1-5, as follows.

Figure 1:
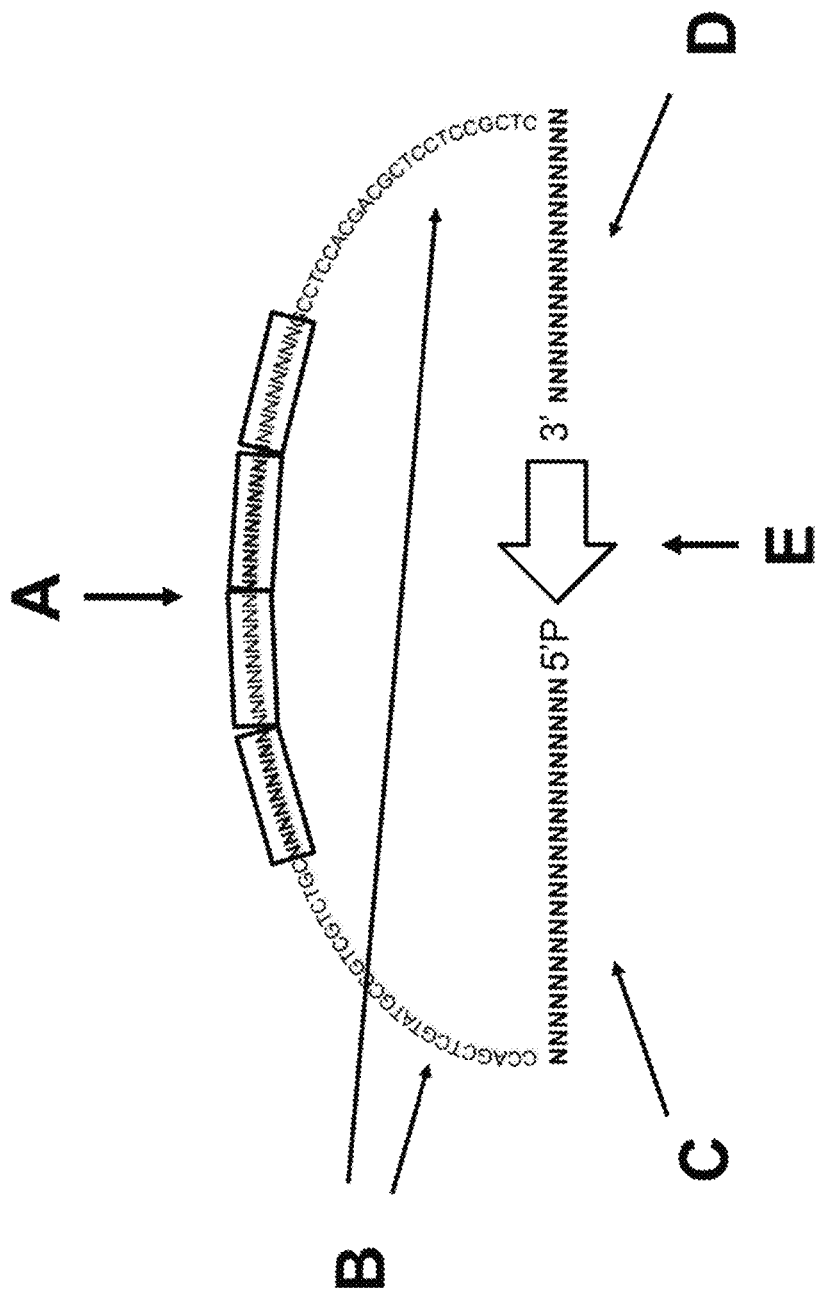
FIG. 1 is a simplified illustration of the padlock.

FIG. 1 shows an example of a padlock of the invention that can also be used as FISH (Fluorescent in situ hybridization) probes. In the core of the padlock, a series of barcodes or barcode regions is implemented which can be used to identify the actual padlock bound to the mRNA by a series of hybridization of fluorescently labeled detector probes that specifically bind to at least one of the barcode regions (A). The core of the padlock i.e. the oligonucleotide may also contain a universal binding site (B) for the binding of a primer used by the polymerase for the rolling circle amplification step (RCA). If selective RCA is used, specific primers that binds to one of the barcode region are used.

Further, FIG. 1 shows the possible priming sites (C & D) for non-selective RCA and the hybridized 5' and the 3' ends of the oligonucleotide to complementary parts of the at least one RNA or c-DNA strand. The gap (E) created between the 5' and the 3' end of the padlock may be 0 to 500, preferably less than 200.

Figure 2:
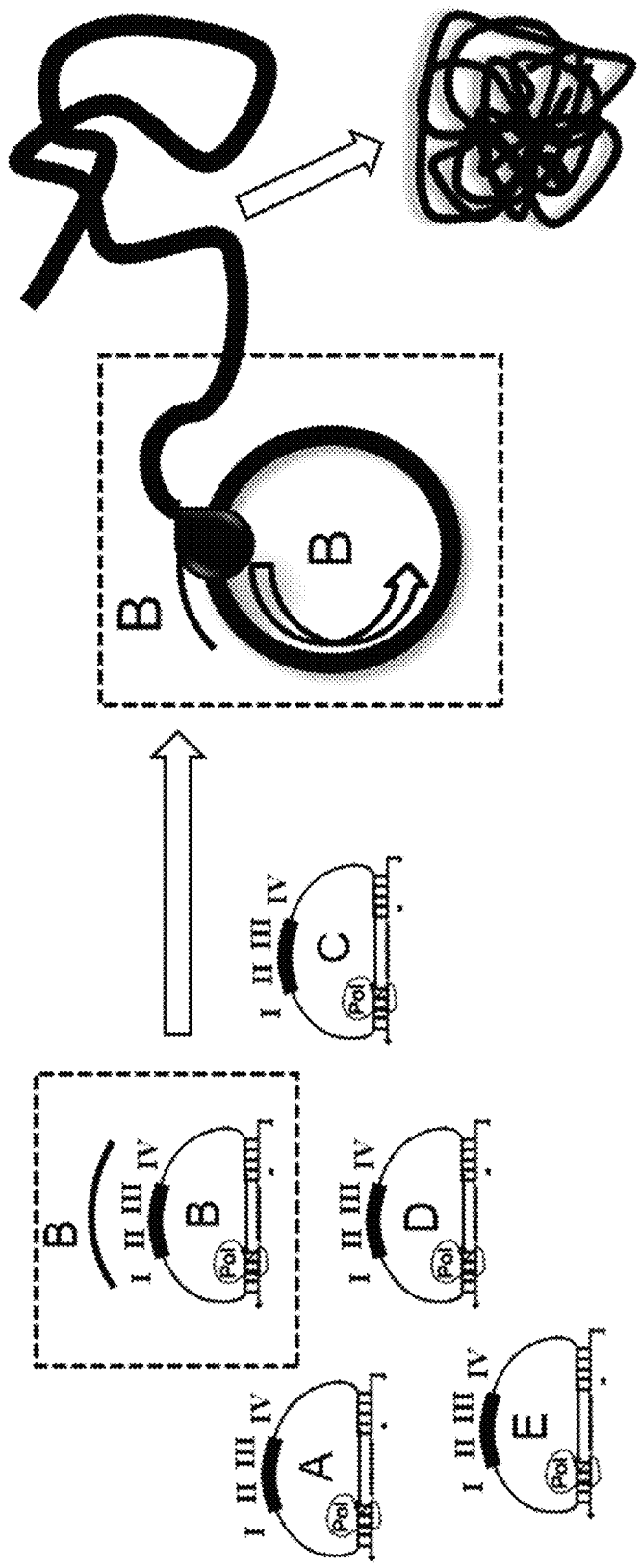
FIG. 2 shows a pool of various circularized padlock oligonucleotides.

FIG. 2 shows a pool of various circularized padlock oligonucleotides for which spatial information exists are used in selective/targeted RCA using an oligonucleotide that recognize a specific set of barcodes. These oligonucleotides act as primers for the RCA reaction and DNA nanoballs/rolonies can be amplified from only selected circularized padlocks. The specific amplification step is shown in FIG. 2, where a pool of various single strand circular templates for which spatial information has already been obtained are used in selective/targeted RCA using short oligonucleotide primers that recognize a specific set of barcodes. These short oligonucleotides act as primer for the RCA reaction and DNA nanoballs/rolonies are generated only from selected and primed circularized padlocks. In the shown example, only single strand circular template marked with (B) is amplified.

Figure 3:
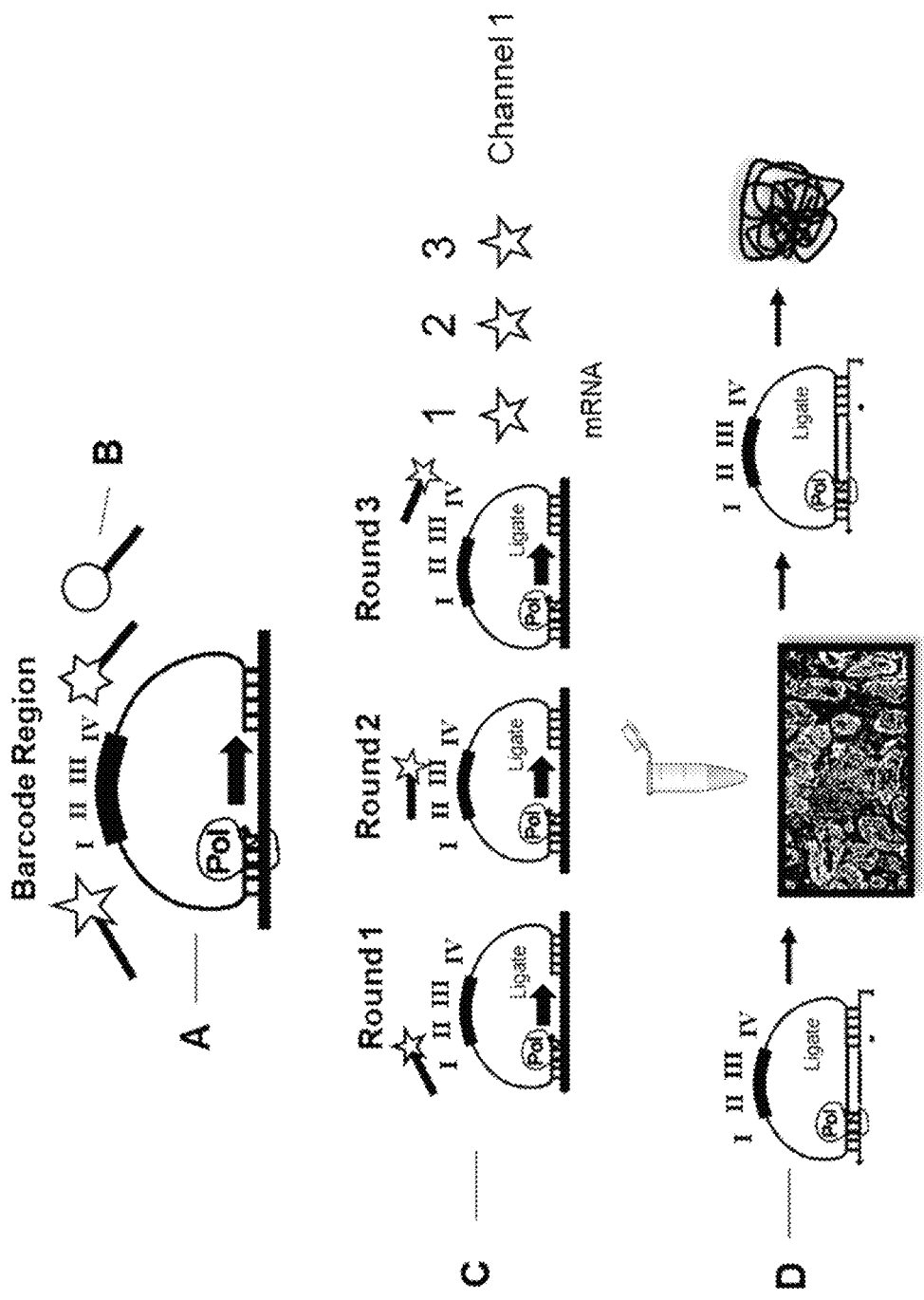
FIG. 3 shows the gap-fill padlock probe technology.

FIG. 3 shows the gap-fill padlock probe technology using probes that is hybridized to a specific portion of a messenger RNA directly on a section of tissue that has been fixed and permeabilized. (A) the oligonucleotide forming a paddock after hybridization and (B) the identification of the actual padlock bound to the mRNA using fluorescently labeled detection probes complementary to the barcode region. (C) The gap-fill region is the sequence of interest on the mRNA, and the gap between the two ends of the probe is filled by the reverse polymerase from the 5' end using the target mRNA as the guide. Following the filling of the gap, the extended hybridized padlock is probed by sequential hybridization of fluorescently labeled detector probes binding to specific internal barcodes (1-4). Each extremity of the padlock are ligated creating a circular molecule. (D) The circularized DNA is either extracted and amplified in tube or directly amplified on fixed tissue using specific rolony primers to selectively generate rolonies that will be sequenced based on expression profiling.

Figure 4:
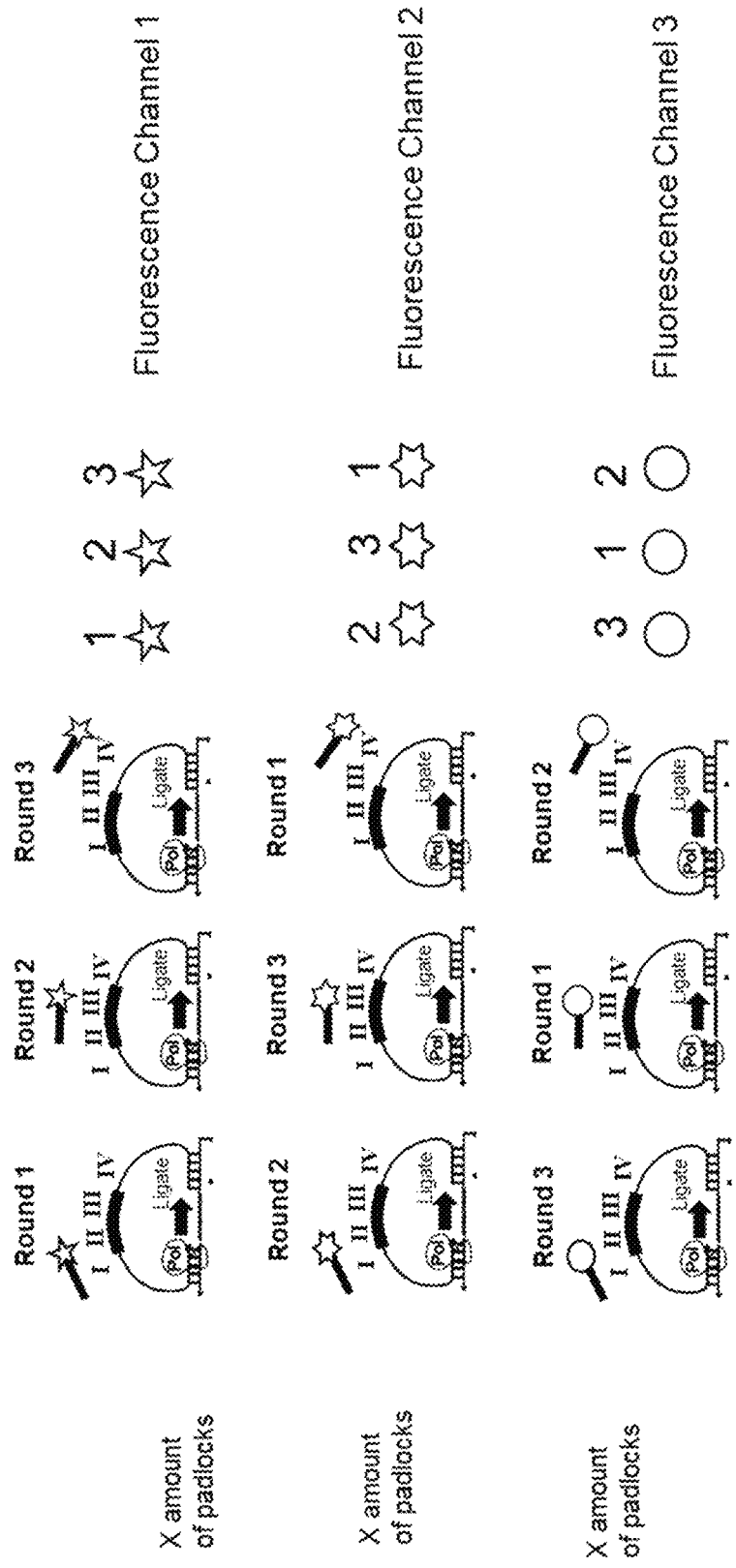
FIG. 4 shows example of the steps allowing the identification of the hybridized padlock oligonucleotides.

FIG. 4 shoes example of the steps allowing the identification of the hybridized padlock oligonucleotides following the filling of the gap. The hybridized padlock for which the gap has been filled is probed by a sequential hybridization of fluorescently labeled detector probes binding to specific internal barcodes. This probing can be done with a subset of padlock oligonucleotides each containing different barcode regions. The binding of the detection probes to the barcode region allow for identification of the actual padlock bound to the mRNA. In this example the detection probes and subset of padlock oligonucleotides are subdivided in three groups that will be identify with padlock probes that uses three different fluorophores and detected in their respective emission channel. Individual probes are identify based on the actual order to which hybridization step of a giving detector probe is occurring.

Figure 5:
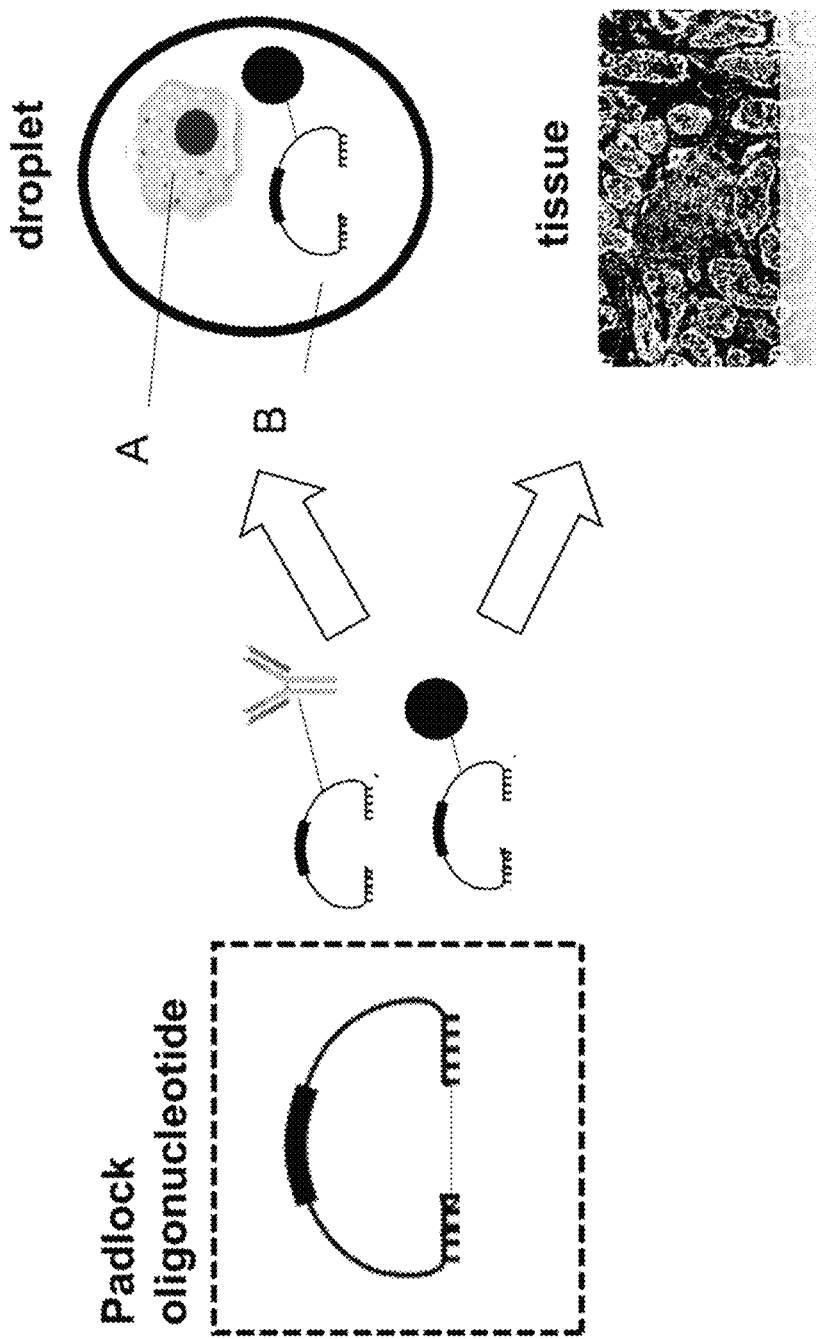
FIG. 5 shows tethered padlock oligonucleotides.

FIG. 5 shows padlock oligonucleotides tethered to beads or linked to an antibody and placed into microdroplets containing (a single cell (A) and a padlock (B)). The padlock can also by incubated in the presence of a tissue section that has been fixed and permeabilized.

Figure 6:
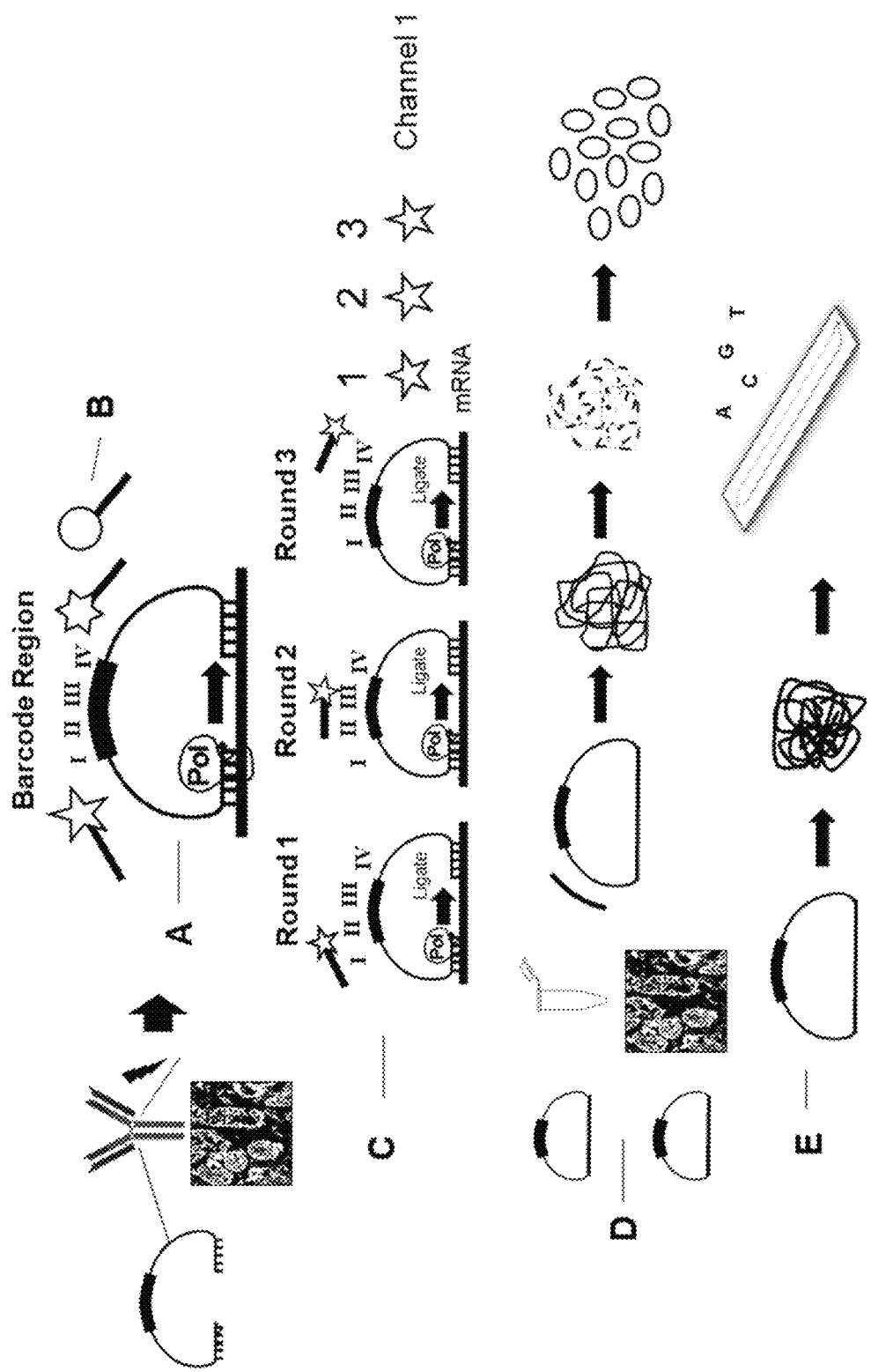
FIG. 6 shows to optional fragmentation and the subsequent amplification of the fragments.

FIG. 6 shows to optional fragmentation of the single strand circular templates and the subsequent amplification of the fragments by rolling circle amplification into a second plurality of DNA concatemers forming rolonies.

Figure 7:
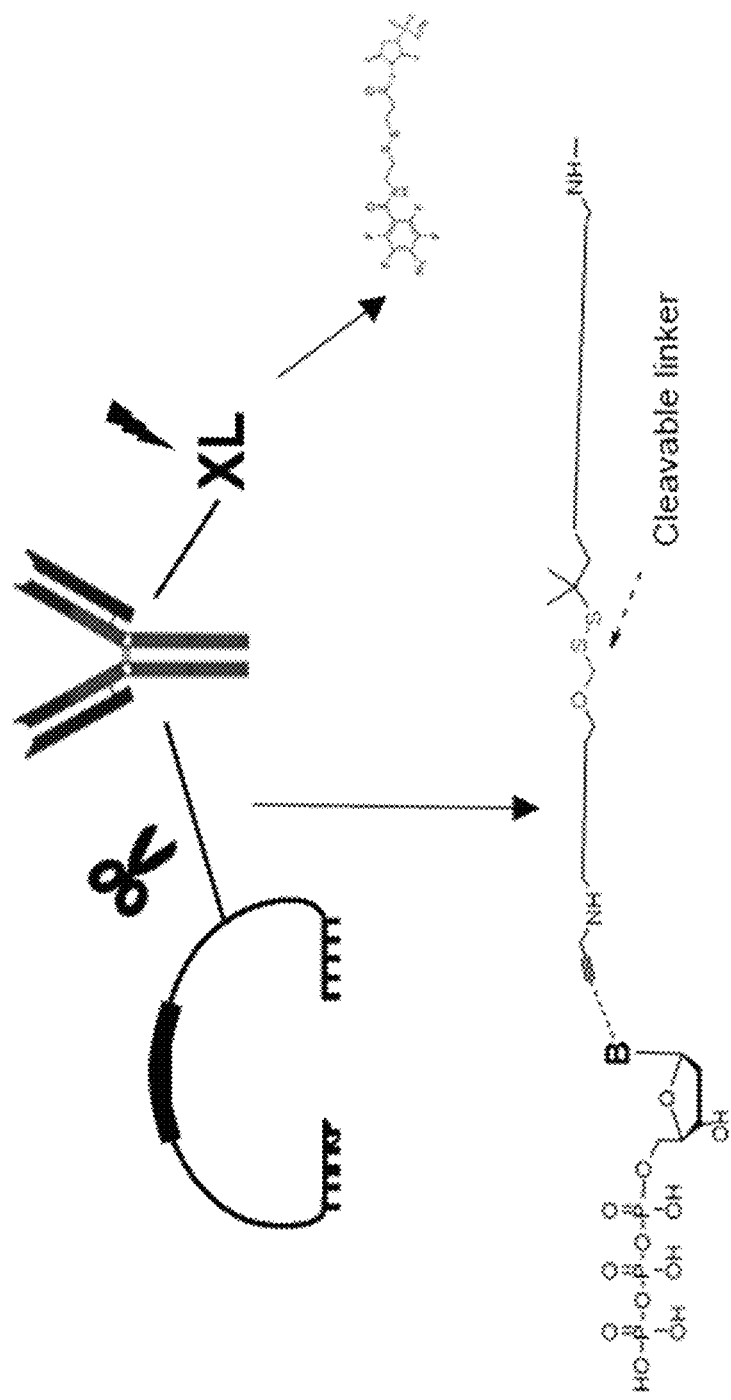
FIG. 7 shows the optional removal of the detection probe

FIG. 7 shows the optional removal of the detection probe from the strand circular templates by using photo-cleavable liker units.

The present method combines the use of oligonucleotide forming a padlock while hybridized (padlock probes) and sequential hybridization for detection of bound probes and sequencing targeted portion of RNA or DNA transcript at a cellular level with less limitation in the amount of transcripts and the length of the sequence that can be analyzed.

In this approach, gap-fill padlock probes containing one or more barcode regions in their core are utilized both as FISH probes and also to capture RNA portion that can be sequenced. Padlock probes have proven very successful in polymerizing short portion of nucleic acids to which it has been hybridized to. Most padlock approaches begin by reverse transcribing the target into cDNA.

The hybridization of the padlock probe to the DNA or RNA strand is followed by a gap-fill step where a reverse polymerase fills the open section between the anchor and the extension side of the padlock from the hybridized 5' portion of the probe using the target mRNA as a guide which is then ligated to from a circular DNA molecule. Alternatively, the padlock can also be hybridized to cDNA which would require additional steps that could be bypassed by targeting the mRNA directly. This technology is known, for example from the already described prior art.

The padlock probes for which the gap has been filled and ligated to form a circular template (the probe can also be filled but ligated only further in the process) are used first as FISH probes or Seq FISH probes using integrated barcoded region in the actual non hybridizing portion of the padlocks detected by labeled oligonucleotides. Finally, the circularized padlock probes are used as a template for rolling circle amplification (RCA) to generate a DNA strand used for sequencing. The thus obtained DNA strands are hereinafter referred to as "rolonies" or "DNA nanoballs". The padlock probes can be detected directly on the tissue or following amplification into rolonies.

The current invention describes a method using the gap-fill padlock where the barcode regions of the padlock oligomers are used to obtain special information or enable further downstream processing of the obtained rolonies and/or a combination thereof.

Detection Probes

The detection probes used in the method of the present invention may by comprised of a) a oligonucleotide with 2 to 20 nucleotides capable of binding to at least a part of the barcode region and b) a detection region selected from the group comprising a magnetic particle, a fluorescence dye, a radioactive label.

Preferable, the detection probes comprise fluorescent dyes known from the art of immunofluorescence technologies, e.g., flow cytometry or fluorescence microscopy. Useful fluorescent moieties might be protein-based, such as phycobiliproteins, polymeric, such as polyfluorenes, small organic molecule dyes, such as xanthenes, like fluorescein, or rhodamines, cyanines, oxazines, coumarins, acridines, oxadiazoles, pyrenes, pyromethenes, or metallo-organic complexes, such as Ru, Eu, Pt complexes. Besides single molecule entities, clusters of fluorescent proteins or small organic molecule dyes, as well as nanoparticles, such as quantum dots, upconverting nanoparticles, gold nanoparticles, dyed polymer nanoparticles can also be used as fluorescent moieties.

Further, the detection region may comprise a radioactive label, for example in the form of radioisotope labeling by exchanging non-radioactive isotopes for their radioactive counterparts, such as tritium, 32P, 35S or 14C, or introducing covalently bound labels, such as 125I, which is bound to tyrosine, 18F within fluorodeoxyglucose, or metallo-organic complexes, i.e. 99Tc-DTPA.

In a variant of the invention, the detection probe is provided with a photo-crosslinkable unit capable of photo-crosslinking the single strand circular template during or after step c) with the sample upon irradiation with light.

The cross-linking agents used in the present invention may be those known from the art of oligonucleotide capture on solid surface or tissue, e.g.,microarray generation, protein:protein interactions, isolating cell surface proteins and preparing labeled probes. Useful moieties might comprised crosslinkers and labeling reagents that contain aryl azide or diazirine functional groups that are capable reacting to form covalent bonds between the antigen binding moiety other molecules when activated by ultraviolet light.

Padlock Oligonucleotides

As shown in FIG. 1, the oligonucleotide has a 5' and a 3' end recognizing a region of interest comprising around 50-1000 nucleic acids, preferable 50 to 200 nucleic acids and further at least one, preferably 1 to 4 barcode regions, each comprising 2-20 nucleotides. Each of the barcode region containing a different sequence.

The padlock probes can for example be attached to an antigen recognizing moiety which can bind to cell specific antigens on a tissue section mounted on a solid surface and can be cross-linked prior to tissue permeabilization as shown of FIG. 5.

Optionally, the detection probe can be removed from the single strand circular template after step c) by for example chemical or photo-cleavage.

In the method of the invention, the padlock oligonucleotides are circularized and the single strand circular template that is generated is replicated by a polymerase capable of rolling circle amplification into a plurality of DNA concatemers forming a DNA nanoball or rolony. For this purpose, the oligonucleotide used in the present invention may comprise at least one primer region with 5 to 50 nucleotides for the rolling circle amplification.

In one embodiment of the invention, the least one primer region is located between the barcode region and the 5' and/or the 3' ends of the oligonucleotide. This embodiment is utilized if the single strand circular template shall be replicated non-selectively using oligonucleotides complementary to the padlock primer region as priming site for the rolling circle amplification polymerase.

In another embodiment of the invention, the least one barcode region is used as primer region. This embodiment is utilized if the single strand circular template is replicated selectively by using oligonucleotides complementary to the barcode region as priming site for the rolling circle amplification polymerase.

Method

As shown in the upper part of FIG. 6, the antigen binding moieties carrying the padlock oligonucleotides can be cross-linked to the tissue and the padlocks can then be released from the moiety.

The gap-fill padlock probe technology is used on probes that is hybridized to a specific portion of a messenger RNA directly on a section of tissue that has been fixed and permeabilized. The gap-fill region is the sequence of interest on the mRNA, and the gap between the two ends of the probe is filled by the reverse polymerase (POL) from the 5' end using the target mRNA as the guide (section A).

The padlock probes are either extracted and amplified by RCA in tube or directly amplified on fixed and permeabilized tissue using specific primers to selectively generate rolonies that will be sequenced based on the detection of the probes that actually bound to their target of interest In one embodiment, after step e), the single strand circular templates are sheared into fragments and the fragments are multiplied by a polymerase capable of rolling circle amplification into a second plurality of DNA concatemers forming rolonies.

When amplified on tissue, the rolonies that are extracted can be sheared in small fragments and re-amplified prior to sequencing (Section C right portion and section E)

Shearing processes are known to the person skilled in the art and my include random shearing via ultrasonic or via uracil containing rolonies and USER enzyme (Uracil DNA glycosylase (UDG) and the DNA glycosylase-lyase Endo-nuclease VIII or site-specific restriction sites).

Before or following to the filling of the gap, the extended hybridized padlock is probed by sequential hybridization of fluorescently labeled detector probes binding to specific internal barcodes (1-4), The ligation of each extremity of the padlock creating a circular molecule can occur prior to the probing or after the probing.

The padlock probes are either extracted and amplified in tube or directly amplified on fixed and permeabilized tissue using specific primers to selectively generate rolonies that will be sequenced based on the detection of the probes that actually bound to their target of interest.

The general steps of the invention are shown in FIG. 1. Here, the gap-fill padlock probe technology was used on probes that is hybridized to a specific portion of a messenger RNA directly on a section of tissue that has been fixed and permeabilized. The gap-fill region is the sequence of interest on the mRNA, and the gap between the two ends of the probe is filled by the reverse polymerase (POL) from the 5' end using the target mRNA as the guide (section A).

Following the filling of the gap, the extended hybridized padlock is probed by sequential hybridization of fluorescently labeled detector probes binding to specific internal barcodes (1-4). (section B). The visualization of the detector probes by fluorescent microscopy imaging allows for physical localization of the padlock oligonucleotide on the tissue and to determine the actual identity of the actual padlock bound to the mRNA or cDNA transcript (using padlock as fluorescence in situ hydridization probes (section C).

Finally, each extremity of the padlock are ligated creating a circular molecule. The circularized DNA is either extracted and replicated by rolling circle amplification in a tube or directly on fixed tissue using specific oligonucleotide primers binding to the barcode region to selectively generate solely rolonies that would be of interest to be sequenced (section D).

In FIG. 3, an example of the sequential steps used in the embodiment of the method to detect and identify the padlock. The hybridized oligonucleotide forming a padlock for which the gap has been filled is probed by a sequential hybridization of detector probes binding to specific internal barcodes. This probing can be done using a subset of padlock oligonucleotides each containing different barcode regions. The binding of the detection probes to the barcode region are done sequentially and allow for the identification of the actual padlock bound to the mRNA or cDNA transcript.

In this example, the padlock oligonucleotides targeting various mRNA portion are subdivided in three groups that will be identify with three sets of detection probes each labeled with three different detection portion, preferably fluorophores. Each of these fluorophores can be detected in their respective emission channel.

In a second embodiment, a plurality of detection probes capable of binding to various portion of the barcode regions is provided in a sequential manner wherein a first detection probe is removed after detection before the next detection probe is provided.

The detection probes are provided sequentially in multiple rounds to the padlock to be identified. In this example three rounds are depicted. In round one a mixture of detector probes complementary to the portion I, II-II or IV of the padlock barcode region are provided. Some of the detection probes will hybridize to one of the barcode regions, others will not. The bound probes are detected after each round of hybridization via their respective fluorescence dye in the channel corresponding to their emission spectra. In the subsequent rounds the detector probes mixture is altered and the detection probes bind on different portion the barcode region. Three individual example are shown, with the first individual padlock, the detector probes bind portion I of the padlock barcode region in round 1, portion II-III in round 2 and finally portion IV in round 3. Therefore the detection is positive in round 1, 2 and 3 which indicates for known barcodes the actual padlock that is present. The other two individual probes show positive binding in round 2,3,1 and 3,1,2 respectively and in with different fluorophore labelled probes (different emission spectra and channel detection) allowing the determination of the padlock binding sequence identity and—after sequencing—the sequence of the DNA targeted (DNA in the filled gap).

This embodiment is performed while the actual padlock is still attached to the sample (tissue) and allows to identify the special distribution of the padlocks on tissue. Further, since three different channels are used for detection and that a plurality of probes can be provided during various round of hybridization, the amount of information per channel is reduced thereby enhancing precision of the special information and/or speed of detection.

In a third embodiment, the gap-filled and/or circularized padlocks i.e. the single strand circular templates are released from the tissue after being detected i.e. they are used as seq FISH probes and visualized. In a variant thereof, the padlock probes can be tethered the a paramagnetic bead or to an antigen recognizing moiety via a cleavable (like a photocleavable) linker allowing the padlock the be targeted to certain region of a tissue section or into microdroplets.

This method of the invention is shown in FIG. 5, wherein the Padlock oligonucleotides are tethered to beads or linked to an antigen recognizing moiety and placed into microdroplets containing (a single cell (A) and a padlock (B), upper part of FIG. 5) or on tissue, bottom portion of the FIG. 5. The technology to create droplet of aqueous suspension in a hydrophobic liquid is commonly known for the "single cell sequencing technology".

The term "antigen recognizing moiety" refers to any kind of antibody or fragmented antibody or fragmented antibody derivatives, directed against markers expressed on the cells of the cell sample. The term relates to fully intact antibodies, fragmented antibody or fragmented antibody derivatives, e.g., Fab, Fab¢, F(ab¢)2, sdAb, scFv, di-scFv, nanobodies. Such fragmented antibody derivatives may be synthesized by recombinant procedures including covalent and non-covalent conjugates containing these kind of molecules. Further examples of antigen recognizing moieties are peptide/MHC-complexes targeting TCR molecules, cell adhesion receptor molecules, receptors for costimulatory molecules, artificial engineered binding molecules, e.g., peptides or aptamers which target, e.g., cell surface molecules. Such antigen recognizing moieties antibody directed may be against antigen expressed by the biological specimens (target cells) intracellular, like IL2, FoxP3, CD154, or extracellular, like CD3, CD14, CD4, CD8, CD25, CD34, CD56, and CD133.

In a another embodiment, the probe tethered to beads or an antibody can be used to generate an array on a solid surface.

In a variant of this embodiment, the sample which is preferable a solid tissue like a fresh-frozen tissue section is placed on a covered glass slide containing the padlock forming oligonucleotide that is tethered to a bead or to an antibody. The tissue is fixed and imaged for histological purposes and permeabilized to release mRNA that can bind to adjacent padlock probes, allowing for the capture of gene expression information and later on the sequence information.

In another instance, the oligonucleotide with an antigen binding moiety binds to the regions of the sample presenting the appropriate antigen and wherein only the mRNA from the sample that are located in the vicinity of the region of interest will bind to the padlock oligonucleotide and subjected to the steps a) to f).

In one instance, the padlock are used to generate rolonies (DNA nanoballs) used in sequencing (in situ) as indicated above or can also be sequenced (ex situ). In that case, the padlocks are circularized and removed from the tissue-containing flowcell and the rolonies generated from the padlocks that have captured RNA are sequenced. When the sequenced is performed ex situ, there is less limitation in terms of read length.

In a variant of this embodiment, specific circularized padlocks can be isolated and sorted specifically when tethered to beads or released when tethered to an antibody.

In this variant, specific rolonies can be generated from the bulk released padlocks ex-vivo by using specific primers corresponding to specific barcodes to be recognized for example by the Phi29 enzyme used for RCA allowing for the selective amplification of a subset of transcripts coming from a specific region or that have been tagged as of interest during the probing steps (seq FISH). Finally, the sequenced data are linked back to the area on the tissue where the mRNA or cDNA transcripts interacted with the padlock originally.

The padlock portion that recognizes a region of interest can also be designed to be more universal for recognizing the 3' portion of mRNA where on of the padlock binding site is composed of poly T, and a 5' side that if composed of random n-mer (random hexamer for instance). The padlock portion that recognizes a region of interest can also be designed to have modified nucleotides such as LNA to help bind the target with higher specificity.

Samples to be analysed with the disclosed method may originate from any specimen, like whole animals, organs, tissues slices, cell aggregates, or single cells of invertebrates, (e.g., Caenorhabditis elegans, Drosophila melanogaster), vertebrates (e.g., Danio rerio, Xenopus laevis) and mammalians (e.g., Mus musculus, Homo sapiens). A biological sample may have the form of a tissues slice, cell aggregate, suspension cells, or adherent cells. The cells may be living or dead.

The spatial information of the rolonies i.e. the location of the rolonies on the sample is determined for example by an imaging step. In yet another variant of the method according to the invention, the sample is converted into isolated cells which are then immobilized by trapping in microcavities or by adherence.

Imaging may be performed for example with techniques are known as "Multi Epitope Ligand Cartography", "Chip-based Cytometry" or "Multiomyx", described for example, in EP 0810428, EP1181525, EP 1136822 or EP1224472. In this technology, cells are immobilized and contacted with antibodies coupled to fluorescent moiety. The antibodies are recognized by the respective antigens on the biological specimen (for example on a cell surface) and after removing the unbound marker and exciting the fluorescent moieties, the location of the antigen is detected by the fluorescence emission of the fluorescent moieties. In certain variants, instead of antibodies coupled to fluorescent moieties, antibodies coupled to moieties detectable for MALDI-Imaging or CyTOF can be used. The person skilled in the art is aware how to modify the technique based on fluorescent moiety to work with these detection moieties. The location of the target moieties is achieved by a digital imaging device with a sufficient resolution and sensitivity in for the wavelength of the fluorescence radiation. The digital imaging device may be used with or without optical enlargement for example with a fluorescence microscope. The resulting images are stored on an appropriate storing device like a hard drive, for example in RAW, TIF, JPEG, or HDF5 format.

What is claimed is:

1. A method for single cell gene expression mapping and targeted RNA or c-DNA sequencing of a sample comprising at least one RNA or c-DNA strand comprising the steps
    a. providing an oligonucleotide having a 5' and a 3' end combined by 50-1000 nucleic acids that are complementary to the at least one RNA or c-DNA strand of the sample wherein the oligonucleotide comprises at least one barcode region with 2-20 nucleotides
    b. hybridizing the oligonucleotide at the 5' and the 3' ends to complementary parts of the at least one RNA or c-DNA strand to create a padlock with a gap between the 5' and the 3' end of the padlock
    c. filling the gap of the padlock with the complementary nucleotides and ligating them to generate a single strand circular template and wherein the single strand circular template is provided with at least one detection probe capable of binding to at least a part of the barcode region
    d. multiplying the single strand circular template by a polymerase capable of rolling circle amplification into a plurality of DNA concatemers forming a rolony
    e. determining the spatial localisation of the single strand circular template
    f. determining the sequence of the single strand circular template wherein the detection probe comprises an oligonucleotide with 2 to 20 nucleotides capable of binding to at least a part of the at least one barcode region and a detection region which uses at least one of a magnetic particle, a fluorescence dye, a radioactive label and an antigen binding moiety, and further wherein after step e), the single strand circular template is sheared into fragments and the fragments are multiplied by a polymerase capable of rolling circle amplification into a second plurality of DNA concatemers forming rolonies.

2. The method according to claim 1, wherein the detection probe is provided with a photo-crosslinkable unit capable of photo-crosslinking the single strand circular template during or after step c) with the sample upon irradiation with light.

3. The method according to claim 1, wherein the detection probe is removed from the single strand circular template after step c).

4. The method according to claim 1, wherein at least one primer region is located between the at least one barcode region and the 5' and/or the 3' ends of the oligonucleotide.

5. The method according to claim 1, wherein the single strand circular template is replicated non-selectively using oligonucleotides complementary to a padlock primer region as priming site for the rolling circle amplification polymerase.

6. The method according to claim 1, wherein the at least one barcode region is used as a primer region.

7. The method according to claim 1, wherein the single strand circular template is replicated selectively by using oligonucleotides complementary to the at least one barcode region as priming site for the rolling circle amplification polymerase.

8. The method according to claim 5, wherein a plurality of detection probes capable of binding to the at least one barcode region of the oligonucleotides is provided.

9. The method according to claim 1, wherein a plurality of detection probes capable of binding to different portions of the at least one barcode region is provided in a sequential manner wherein a first detection probe is removed after detection before the next detection probe is provided.

10. The method according to claim 1, wherein the sample comprising at least one RNA or c-DNA strand is provided from a plurality of cells or from a tissue section and wherein before or after step a), the sample is lysed or permeabilized.

11. The method according to claim 1, wherein the oligonucleotide is provided with an antigen binding moiety which binds to the regions of the sample presenting the appropriate antigen and wherein only the mRNA located in the vicinity of that region is bound to the padlock oligonucleotide and subjected to the steps a) to f).

12. The method according to claim 1, wherein the antigen binding moiety or the detection probes are provided with a fluorescence dye and wherein only the regions of the sample bound with the fluorescence dye are subjected to the steps a) to f).

13. The method according to claim 1, wherein the regions of the sample are bound with an antibody and that have released mRNA or cDNA that have been hybridized to a padlock are subjected to light capable of exciting the fluorescence dye and imaging the resulting emission radiation to determine the spatial localization of the single strand circular template.

* * * * *